(12) United States Patent
Ricci

(10) Patent No.: US 11,324,630 B2
(45) Date of Patent: May 10, 2022

(54) CONTROLLED VOLUME DROPPER

(71) Applicant: Dompe' Farmaceutici S.P.A., Milan (IT)

(72) Inventor: Alfredo Ricci, Cappelle sul Tavo (IT)

(73) Assignee: DOMPE' FARMACEUTICI S.P.A., Milan (IT)

(*) Notice: Subject to any disclaimer, the term of this patent is extended or adjusted under 35 U.S.C. 154(b) by 199 days.

(21) Appl. No.: 16/313,514

(22) PCT Filed: Jun. 29, 2017

(86) PCT No.: PCT/IB2017/053906
§ 371 (c)(1),
(2) Date: Dec. 27, 2018

(87) PCT Pub. No.: WO2018/002866
PCT Pub. Date: Jan. 4, 2018

(65) Prior Publication Data
US 2020/0170836 A1    Jun. 4, 2020

(30) Foreign Application Priority Data
Jun. 30, 2016 (IT) .......................... 102016000031850

(51) Int. Cl.
*A61F 9/00* (2006.01)

(52) U.S. Cl.
CPC .................................. *A61F 9/0008* (2013.01)

(58) Field of Classification Search
CPC .......... A61F 9/0008; A61M 2005/3101; B65D 47/18
See application file for complete search history.

(56) References Cited

U.S. PATENT DOCUMENTS

| 772,114 A | 10/1904 | Pappenheim |
| 3,354,882 A | 11/1967 | Coanda |

(Continued)

FOREIGN PATENT DOCUMENTS

| BE | 334512 A | 6/1926 |
| CA | 2106306 A1 | 7/1993 |

(Continued)

OTHER PUBLICATIONS

English Abstract and Machine Translation for French Publication No. 3023172 A, published Jan. 8, 2016, 14 pgs.

(Continued)

*Primary Examiner* — Tatyana Zalukaeva
*Assistant Examiner* — Nhu Q. Tran
(74) *Attorney, Agent, or Firm* — Fredrikson & Byron, P.A.

(57) ABSTRACT

A medical device (100) for the instillation of medical products in droplet form is described, said device comprising a hollow cylindrical body (10) and a rod (20) slidably mobile inside the hollow cylindrical body (10) and provided with a head (21) on which a rubber washer (40) is fixed, which washer, during the sliding of the rod (20), is in contact with an inner surface of the hollow cylindrical body (10). The rod (20) is formed as two portions (22, 24) of different diameter and the device (100) further comprises a sealing bush (30) between the hollow cylindrical body (10) and the rod (20), wherein there is provided a stop (32) which prevents the passage of the portion (22) with a larger circular section of the rod (20).

19 Claims, 4 Drawing Sheets

(56) References Cited

U.S. PATENT DOCUMENTS

| | | | |
|---|---|---|---|
| 3,857,423 A | 12/1974 | Ronca | |
| 4,153,057 A | 5/1979 | Kobel | |
| 4,642,102 A * | 2/1987 | Ohmori | A61M 5/31555 604/210 |
| 5,217,433 A | 6/1993 | Bunin | |
| 5,685,845 A | 11/1997 | Grimard | |
| 5,692,644 A | 12/1997 | Gueret | |
| 5,964,043 A | 10/1999 | Oughton et al. | |
| 6,112,779 A | 9/2000 | Camilla | |
| 6,258,078 B1 | 7/2001 | Thilly | |
| 7,429,483 B2 | 9/2008 | Lambiase | |
| 7,563,256 B2 | 7/2009 | Hearne | |
| 2001/0021828 A1* | 9/2001 | Fischer | A61M 5/31511 604/218 |
| 2006/0049127 A1 | 3/2006 | Katz et al. | |
| 2007/0181449 A1 | 8/2007 | Ghinelli | |
| 2008/0108045 A1 | 5/2008 | Hamamoto et al. | |
| 2008/0314775 A1 | 12/2008 | Owoc | |
| 2010/0145282 A1 | 6/2010 | Hansen et al. | |
| 2010/0179487 A1* | 7/2010 | Woehr | A61M 5/326 604/196 |
| 2011/0190709 A1 | 8/2011 | Mitsuno et al. | |
| 2012/0232492 A1 | 9/2012 | Hato | |
| 2013/0184677 A1 | 7/2013 | Py | |
| 2014/0008366 A1 | 1/2014 | Genosar | |
| 2014/0012227 A1* | 1/2014 | Sigg | A61K 9/0048 604/506 |
| 2015/0101705 A1 | 4/2015 | Kim | |
| 2015/0105734 A1 | 4/2015 | Bryant et al. | |
| 2016/0144109 A1* | 5/2016 | Stroup | A61M 39/12 604/248 |

FOREIGN PATENT DOCUMENTS

| | | | |
|---|---|---|---|
| CN | 1229395 A | 9/1999 | |
| CN | 1259859 A | 7/2000 | |
| CN | 2411782 Y | 12/2000 | |
| CN | 1756573 A | 4/2006 | |
| CN | 2880125 Y | 3/2007 | |
| CN | 101516526 A | 8/2009 | |
| CN | 201444781 U | 5/2010 | |
| CN | 202113430 U | 1/2012 | |
| CN | 103124540 A | 5/2013 | |
| CN | 202982801 U | 6/2013 | |
| EP | 0459182 A2 | 12/1991 | |
| EP | 723921 A2 | 7/1996 | |
| EP | 1009356 A1 | 6/2000 | |
| FR | 2427960 A1 | 1/1980 | |
| FR | 3023172 A1 * | 1/2016 | A61M 5/31513 |
| FR | 3023172 A1 | 1/2016 | |
| JP | 2006213332 A | 8/2006 | |
| JP | 2011519587 A | 7/2011 | |
| JP | 2013530014 A | 7/2013 | |
| TW | 201402165 A | 1/2014 | |
| WO | 0164266 A1 | 9/2001 | |
| WO | 2014164419 A1 | 10/2014 | |
| WO | 2014164685 A1 | 10/2014 | |

OTHER PUBLICATIONS

English Abstract for Chinese Publication No. 20113430 U, published Jan. 8, 2012, 1 pg.
English Abstract for Chinese Publication No. 202982801 U, published Jun. 12, 2013, 1 pg.
English Abstract for Taiwan Publication No. 201402165 A, published Jan. 16, 2014, 1 pg.
PCT International Search Report and Written Opinion dated Sep. 22, 2017 for Intl. App. No. PCT/IB2017/053906, from which the instant application is based, 10 pgs.
Search Report and Written Opinion dated Mar. 3, 2017 for related Italian App. No. 102016000031850, 12 pgs.

* cited by examiner

Sec. III-III

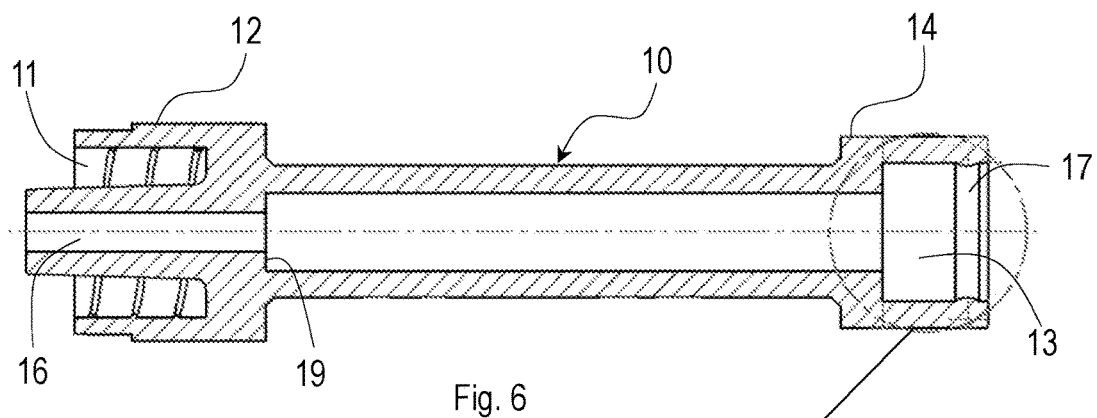
Fig. 6
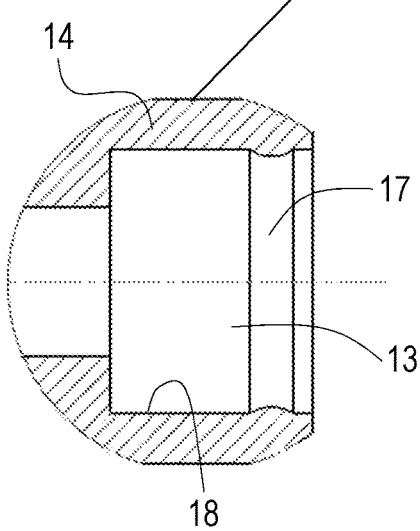
Fig. 6a
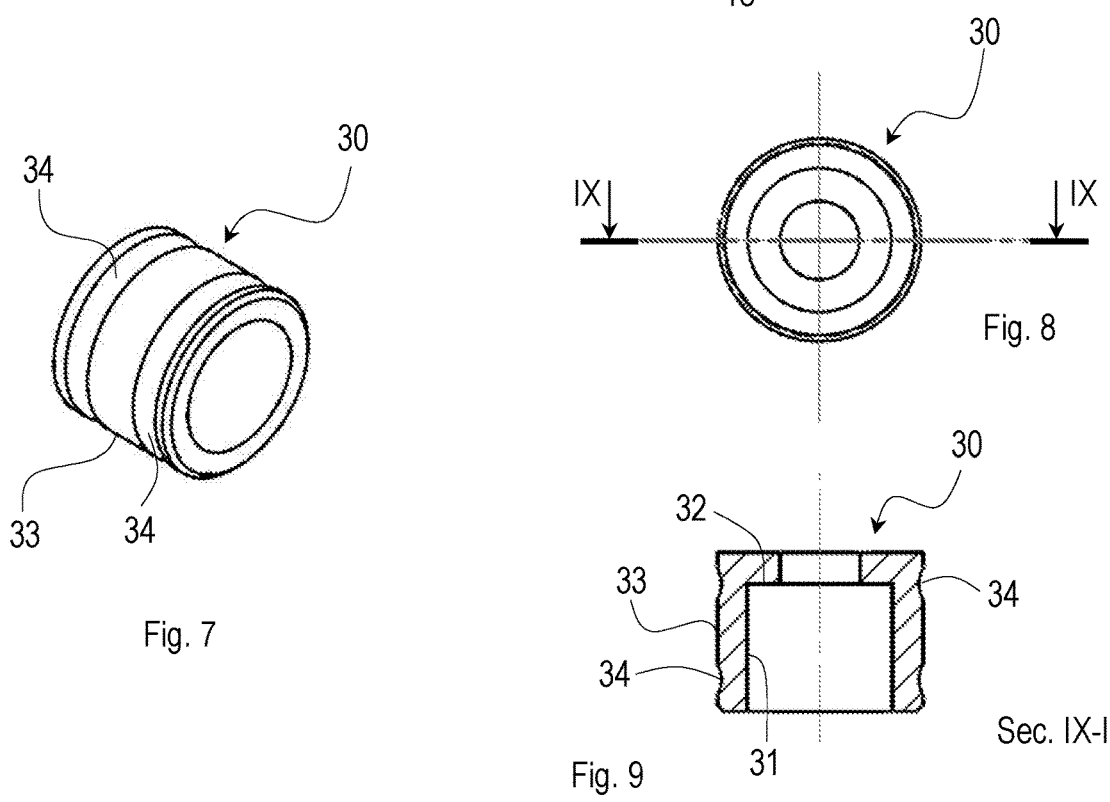
Fig. 7
Fig. 8
Fig. 9
Sec. IX-IX

Sec. XIII-XIII

CONTROLLED VOLUME DROPPER

RELATED APPLICATIONS

This application is a 35 U.S.C. 371 national stage filing from International Application No. PCT/IB2017/053906, filed Jun. 29, 2017, which claims priority to Italian Application No. 102016000031850, filed Jun. 30, 2016, the teachings of which are incorporated herein by reference.

FIELD OF THE INVENTION

The present invention relates to a dropper or syringe device for instilling medical products in small doses and for drawing off medical liquids from bottles on which an adapter for a Luer lock fitting may be mounted. More particularly the present invention relates to a controlled volume dropper.

The field of application of the invention is that regarding medical instruments for the application of drugs, in particular eye solutions, by means of instillation. In detail, the controlled volume dropper according to the invention comes under the category of those droppers which are formed by a hollow cylindrical body, inside which a sealed plunger slides, and which inject or draw fluids in the human body.

The controlled volume dropper is a device which aspirates and administers, but does not inject, a relatively small and predetermined volume of medical product. The invention allows the administration of small doses of fluid, which would require a cross-section of the cylinder/reservoir too small to be handled, using a syringe of common dimensions.

As is known in the art, the operating principle of syringe injectors is well documented, but here the relevant state of the art is that concerning syringes to which a system for mechanical control of the volume of administered fluid is applied.

BACKGROUND OF THE INVENTION

The state of the art is represented by a large number of inventions and solutions aimed at obtaining the dispensing of a controlled volume of fluid.

Document CN 2021 13430U proposes a double volumetric chamber, with the second chamber having a slimmer and graduated section. Patent CN 202982801 U proposes a similar solution in which however the two reservoirs are contained in the same cylinder. Patent TW 201402165A introduces a mechanical stop which limits, in advance, the stroke of the plunger, determining the volume of liquid to be injected. Patent WO2014/164419 consists of the "fusion" of the two systems, having a double chamber and a mechanical stop of the plunger. Similarly, WO 2014/164685, as well as representing a similar volumetric control system, places the two reservoirs in communication, one inserted inside the other, so that the pressure of the fluid between the two chambers remains constant.

Most of the systems present on the market have two major drawbacks:
  Despite the fact they have to instill small controlled volumes they are bulky, complex to operate and not easy to handle. In short, they do not allow use with one hand only.
  The second drawback is that they are devices which are complex to assemble. Assembly of the parts results in high production costs and, given their complexity, the parts are subject to misalignment, losing the capacity for operation and making use difficult.

SUMMARY OF THE INVENTION

The main object of the present invention is to provide a dropper configured so as to overcome, or at least reduce, the drawbacks stated above with reference to devices of the known type.

More particularly the present invention overcomes these drawbacks in that:
  it functions like a normal syringe which instills droplets of product and can be operated with three fingers;
  it is made up of mechanical elements—cylinder, rod and bearing surfaces or stops—that are perfectly matching, free from play or joints which may deteriorate with use;
  it allows the drug to be easily drawn from its container.

According to the invention a medical device is therefore provided for the instillation of medical products, in particular ophthalmic products, in droplet form, comprising:
  a hollow cylindrical body;
  a rod, slidably mobile inside the hollow cylindrical body and provided with a head on which a rubber washer is fixed, which washer, during sliding of the rod, is in contact with the inner surface of the hollow cylindrical body.

The device is characterized in that the rod is formed as two portions of different diameter and in that it comprises a sealing bush between the hollow cylindrical body and the rod, wherein there is provided a stop which prevents the passage of the portion with a larger circular section of the rod.

Moreover the device has, in the Luer lock zone, instead of a cylindrical surface, bevelled flat faces, so that the side surface is not round but polygonal. This shape increases considerably the grip for the patient who has to "screw" the dropper into an adapter in order to perform removal of the drug and subsequent instillation thereof in the eye.

BRIEF DESCRIPTION OF THE DRAWINGS

Further features and advantages of the invention will become clearer from the description of a preferred, but not exclusive embodiment of a dropper or syringe device according to the present invention, illustrated by way of a non-limiting example in the accompanying drawings, in which:

FIG. 6 is a longitudinally sectioned view of the hollow cylindrical body of FIG. 5.

FIG. 6a is a detailed view of the detail shown encircled in FIG. 6.

FIG. 7 is a perspective view of the sealing bush of the device according to the invention.

FIG. 8 is a rear view of the sealing bush of FIG. 7.

FIG. 9 is a cross-sectional view, along line IX-IX of FIG. 8.

DETAILED DESCRIPTION OF A PREFERRED EMBODIMENT OF THE INVENTION

Figure 1:
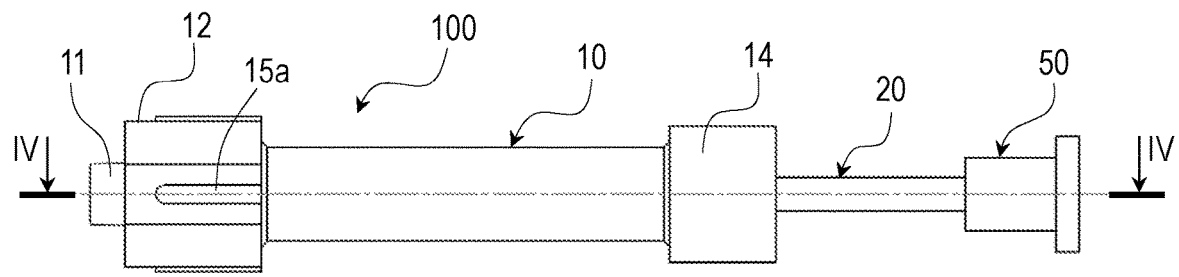
FIG. 1 is a side view of the device according to the invention, in the fully open position, or position where the rod is fully retracted from the hollow cylindrical body.
Figure 2:
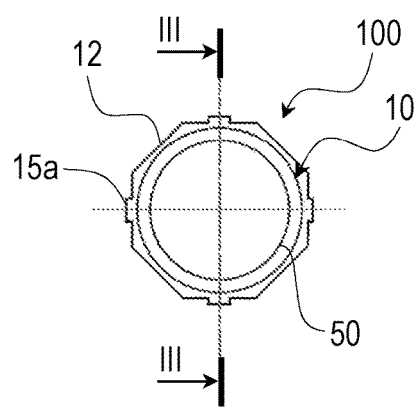
FIG. 2 is a rear view of the device of FIG. 1, in the fully closed position, or position where the rod is fully inserted inside the hollow cylindrical body.

The invention will be described here below by way of an illustrative but non-limiting example, with particular reference to some illustrative embodiments.

The invention consists of a device, hereinafter referred to as dropper, with can be used to draw and supply or instill a small known and predetermined quantity of a medical product.

With reference to FIGS. 1 to 4, the dropper, denoted in general by reference numeral 100, comprises a hollow cylindrical body 10 and a rod 20, slidably mobile inside the hollow cylindrical body 10.

The hollow cylindrical body 10 has a front end portion 12 and a rear end portion 14, each of which has an external diameter greater than the external diameter of the hollow cylindrical body 10.

The front end portion 12 is provided with a Luer lock fitting 11 and has an internal diameter smaller than the internal diameter of the hollow cylindrical body 10. The internal diameter of the front end portion 12 preferably tapers in a funnel shape, thereby defining a passage 16 for the exit of one or more drops of medical liquid to be instilled. At the front end portion 12, in the inner surface of the hollow cylindrical body 10, there is provided a bearing surface or mechanical stop 19 which can be seen in FIG. 6.

Figure 5:
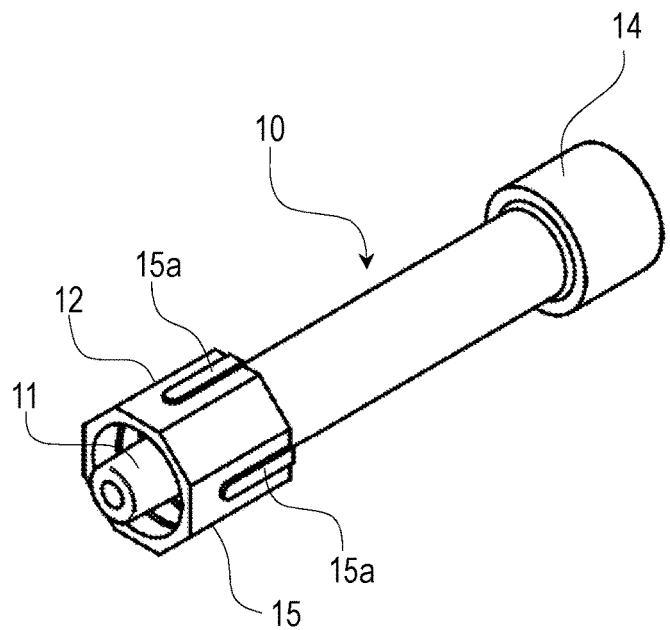
FIG. 5 is a perspective view of the hollow cylindrical body of the device according to the invention, which shows in detail the polygonal gripping surface in the Luer lock fitting zone.

Preferably, and as shown in detail in FIG. 5, the front end portion 12 of the hollow cylindrical body 10 has a faceted outer surface 15 with a preferably octagonal cross-section. This particular form of the outer surface 15 improves, advantageously, gripping of the Luer lock fitting by a user, during engagement/disengagement of the dropper 100 onto/from a corresponding Luer lock adapter provided on the opening of a bottle or vial containing the medical liquid, for example an eye solution, which is to be drawn and subsequently instilled in the eye.

In a preferred embodiment, one or more faces of the faceted outer surface 15 are provided with ridges 15a, preferably four ridges 15a formed on alternating faces of the faceted outer surface 15.

Referring to FIG. 6, the rear end portion 14 has an internal diameter greater than the internal diameter of the hollow cylindrical body 10, so as to define a seat 13 for the housing of a sealing bush 30—shown in detail in FIGS. 7 to 9—which will be described in detail here below.

Figure 10:
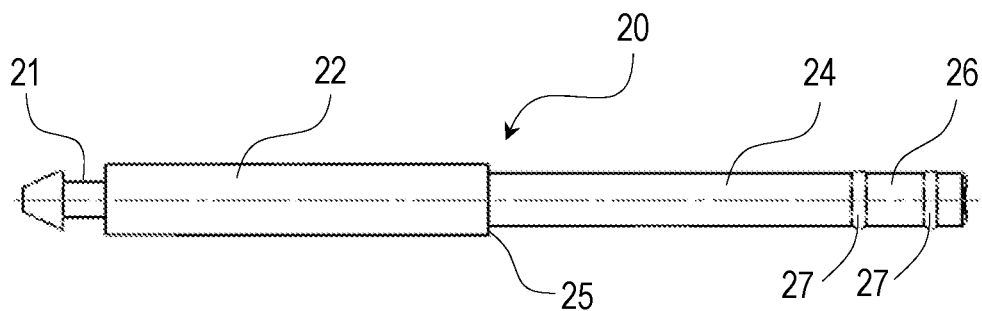
FIG. 10 is a side view of the rod of the device according to the invention.

As shown in greater detail in FIG. 10, the rod 20 of the dropper 100 is provided with two portions. More particularly the rod 20 has a first portion 22 with a larger circular section and a second portion 24 with a smaller circular section. The first and the second portions 22, 24 of the rod 20 are such that the first portion 22 cannot come out of the hollow cylindrical body 10, while the second portion 24 can slide in and out of the hollow cylindrical body 10 during the stroke of the rod 20. At the transition zone between the first portion 22 and the second portion 24 of the rod 20 there is therefore a shoulder 25, the function of which will become clearer in the following of the present description.

Figure 3:
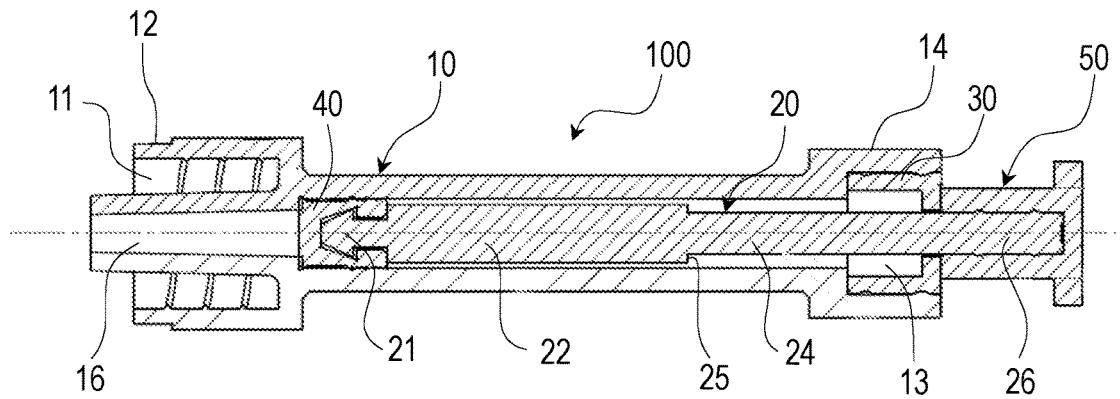
FIG. 3 is a cross-sectional view, along line III-Ill of FIG. 2.
Figure 4:
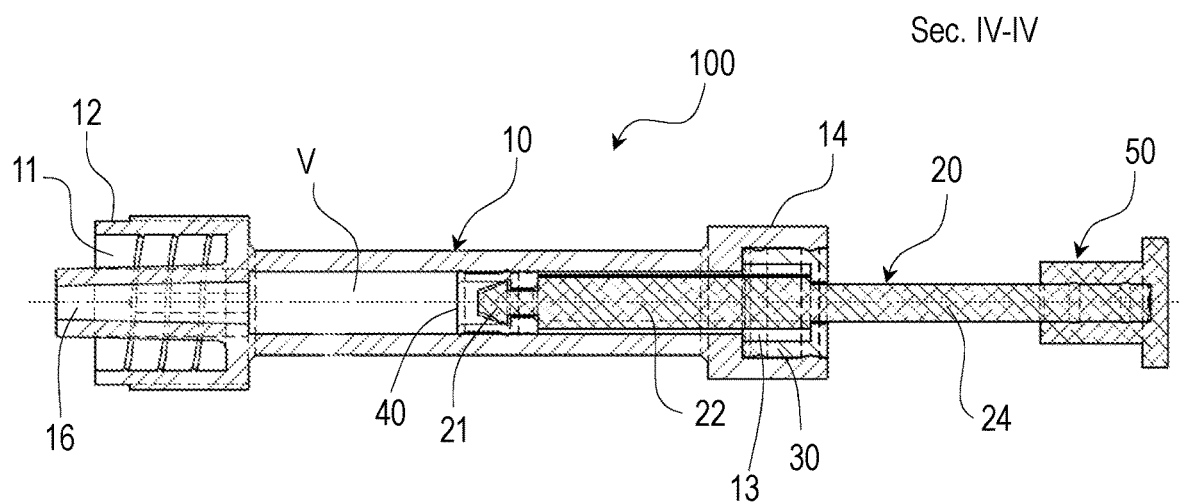
FIG. 4 is a cross-sectional view, along line IV-IV of FIG. 1.

The rod 20 also has a head 21, extending from the portion 22 with a larger circular section, on which a rubber washer 40 is fixed, for example interlocked or glued (FIGS. 3 and 4). During the stroke of the rod 20 inside the hollow cylindrical body 10, the rubber washer 40 stays in contact with the inner surface of the hollow cylindrical body 10 and in the position of total closure of the dropper 100—shown in FIG. 3—the rubber washer 40 abuts against the bearing surface 19 of the hollow cylindrical body 10.

As shown in greater detail in FIGS. 7 to 9, the sealing bush 30 has an external diameter substantially the same as the internal diameter of the rear end portion 14 of the hollow cylindrical body 10. The sealing bush 30 has also an inner surface 31 provided with a bearing surface or mechanical stop 32, against which, during use of the dropper 100, the shoulder 25 of the rod 20 can abut, as will become clearer here below.

Moreover, at an outer surface 33 thereof, the sealing bush 30 has at least one groove 34, preferably an annular groove, configured to interlockingly couple with a corresponding rib or ridge 17 formed on an inner surface 18 of the seat 13 of the rear end portion 14 of the hollow cylindrical body 10. In the embodiment illustrated in the drawings a pair of annular grooves 34 and a rib 17 are provided. Alternatively it is possible to provide at least one rib or ridge on the sealing bush 30 and corresponding grooves in the hollow cylindrical body 10.

This interlocking coupling between the sealing bush 30 and the hollow cylindrical body 10 facilitates, advantageously, the mode of assembly of these two components, and therefore of the dropper 100 according to the invention.

The rod 20 is stopped, during its stroke, by the sudden variation in cross-section or bearing surface 25 between the first portion 22 and the second portion 24, which is marked and without connecting radii, and by the sealing bush 30.

Owing to this particular shape thereof and to the presence of the sealing bush 30, the rod 20 cannot come out completely from the hollow cylindrical body 10 of the device 100, since, during total opening of the dropper 100, shown in FIG. 4, the first portion 22 with a larger circular section of the rod 20 encounters the sealing bush 30, in particular its bearing surface or mechanical stop 32, which is such as to allow only the second portion 24 with a smaller circular section of the rod 20 to pass, but not that with a larger circular section 22.

The first portion 22 with larger circular section of the rod 20 has a predetermined length. In this way an internal volume V of the hollow cylindrical body 10 is defined. Typically the predefined internal volume V of the hollow cylindrical body 10 is equal to approximately 2-3 drops of medical liquid, i.e. about 135 mm$^3$.

The sudden variation in cross-section of the rod 20 and the bearing surface or mechanical stop 32 of the sealing bush 30 determine therefore a mechanical stop which limits the maximum aspiration of medical product and allows the creation of a mechanical bearing surface between the rod 20 and the sealing bush 30.

Moreover the narrowing of the cross-section of the rod 20, together with the sealing bush 30, allows a reliable and repeatable mechanical bearing surface to be obtained, this also being simple to realize.

Furthermore, during the sliding movement of the rod 20 inside the hollow cylindrical body 10, there is controlled friction between the rubber washer 40 and the inner surface of the hollow cylindrical body 10. This function is of great importance for regulating the flow of the single drops which must be instilled. The rubber washer 40, placed in contact with the hollow cylindrical body 10 and interlocked with the rod 20, performs this function.

Figure 11:
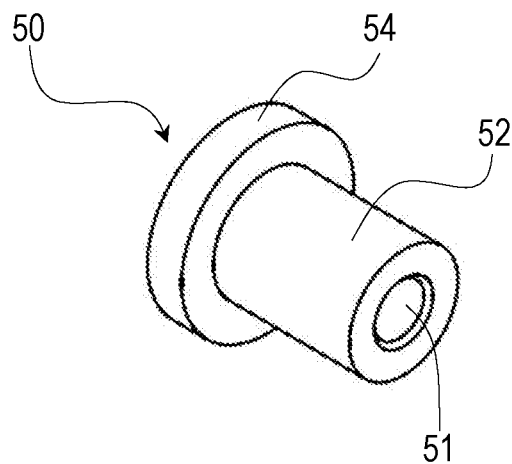
FIG. 11 is a perspective view of a slider of the device according to the invention.
Figure 12:
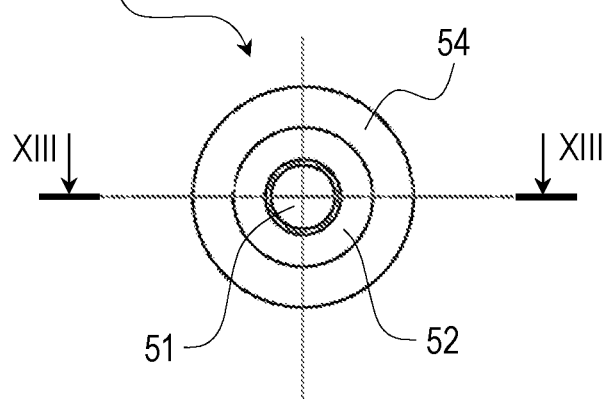
FIG. 12 is a front view of the slider of FIG. 11.
Figure 13:
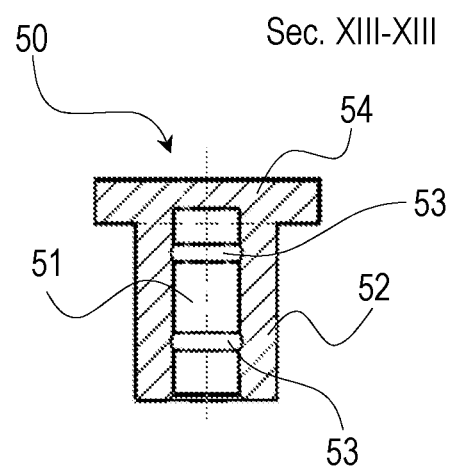
FIG. 13 is a cross-sectional view, along line XIII-XIII of FIG. 12.

The dropper 100 further comprises a slider 50, shown in detail in FIGS. 11 to 13, which is interlockingly coupled on the free end 26 of the second portion 24 with a smaller circular section of the rod 20 (FIG. 3).

During use the slider 50 is configured to be grasped, with three fingers, by the user of the dropper 100 so as to operate the rod 20 inside the hollow cylindrical body 10 and draw and subsequently instill a quantity of eye solution inside the eye.

The slider 50 comprises, in particular, a hollow—preferably cylindrical—body 52 from which a flange 54 extends. The hollow body 52 defines a seat 51 for housing the free end 26 of the second portion 24 with a smaller circular section of the rod 20.

An inner surface of the seat 51 is provided with at least one groove, preferably an annular groove, in the embodiment a pair of annular grooves 53, configured to interlockingly couple with respective ribs 27 formed on the free end 26 of the rod 20. This interlocking coupling between the rod 20 and the slider 50 facilitates, advantageously, the mode of assembly of these two components, and therefore of the dropper 100 according to the invention. Alternatively, it is possible to provide at least one rib on the free end 26 of the second portion 24 with a smaller circular section of the rod 20 and corresponding grooves on the inner surface of the seat 51 of the slider 50.

With reference to FIGS. 3 and 4, it is now disclosed the operation of the dropper 100 according to the invention.

Here below reference will be made to an ophthalmic liquid, but it is understood that entirely the same considerations are applicable in the case of any other medical liquid which is to be instilled.

It is assumed that a user must instill a predetermined quantity of eye solution, typically 2-3 drops, in his/her eye. In the initial state the dropper 100 is in its completely closed position, shown in FIG. 3, with the rubber washer 40 abutting against the bearing surface or mechanical stop 19 of the hollow cylindrical body 10. First of all the user couples the Luer lock fitting 11 of the dropper 100 with a Luer lock adapter (not shown) provided on the mouth of a vial (not shown) containing the eye solution to be instilled. This coupling operation is facilitated by the faceted form of the outer surface 15 of the front end portion 14 of the hollow cylindrical body 10.

Subsequently the user, by acting on the slider 50 of the dropper 100, retracts the rod 20 inside the hollow cylindrical body 10, until the shoulder 25 of the rod 20 abuts against the bearing surface or mechanical stop 32 of the sealing bush 30. This condition is shown in FIG. 4. Following this retracting movement the volume V of the hollow cylindrical body 10 is filled with the predetermined quantity of eye solution. Once the quantity of eye solution necessary has been drawn from the vial, the user disengages the dropper from the vial and then proceeds with instillation of the eye solution in the eye. For this purpose, he or she acts again on the slider 50, exerting a pushing force on it so as to move the rod 20 forwards inside the hollow cylindrical body 10, until the rubber washer 40 abuts against the bearing surface or mechanical stop 19 of the hollow cylindrical body 10, with consequent complete instillation of the eye solution (FIG. 3). The operation of instillation can then be considered terminated.

ADVANTAGES OF THE INVENTION

In the tests carried out, using prototypes, the controlled volume dropper demonstrated considerable ease of use and excellent duration of the functional and mechanical features over a prolonged period of time.

The manufacturing and assembly costs are extremely low.

These two elements in combination, that is ease of use and low cost, make diffusion and marketing of the controlled-volume dropper relatively easy.

The device is held with only three fingers. The dimensions of the device have been specifically designed for this purpose. Moreover the movement the patient must perform in order to instill a drop in the eye is in the direction of instillation of the drop, i.e. the patient has to press on the slider. Since no lateral forces are imparted to the device, it does not move sideways, does not wobble or change position and allows the patient to perform instillation easily and safely, also at a distance very close to the eye.

From the description provided the features of the dropper forming the subject of the present invention are clear, as are the associated advantages.

Further variations of the embodiment described above are possible, without departing from the teaching of the invention.

Finally it is clear, that the dropper designed in this way may be subject to numerous changes and variations; moreover all the details can be replaced by technically equivalent elements. In practice any materials and dimensions may be used according to technical needs.

The invention claimed is:

1. A medical device for aspiration of small doses of medical product and subsequent administration thereof in droplet form, comprising:
   a hollow cylindrical body; and
   a rod slidably mobile inside the hollow cylindrical body and provided with a head on which a rubber washer is fixed, the rubber washer, during sliding of the rod, being in contact with an inner surface of the hollow cylindrical body;
   wherein the rod is formed as two portions having different diameters, a shoulder being formed at a transition zone between the two portions;
   wherein the device further comprises a sealing bush between the hollow cylindrical body and the rod, the sealing bush providing a first mechanical stop against which the shoulder abuts to prevent passage outside the hollow cylindrical body of one of the two portions of the rod having a larger circular section, wherein the first mechanical stop is adjacent to a rear end of the hollow cylindrical body, the larger circular section of the one portion of the rod having a profile similar to yet smaller diameter than that of the hollow cylindrical body so as to be slidable within the body; and
   wherein when the rod is drawn back to point at which the shoulder abuts the first mechanical stop, the one portion of the rod remains within the hollow cylindrical body, whereby length of the one portion correspondingly sets a maximum volume within the body for the medical product.

2. The device according to claim 1, wherein the hollow cylindrical body has a front end portion having an internal diameter smaller than an internal diameter of the hollow cylindrical body, a second mechanical stop being defined on said front end portion.

3. The device according to claim 2, wherein the one portion with larger circular section of the rod has a stroke limited between said first mechanical stop and said second mechanical stop.

4. The device according to claim 2, wherein the front end portion has an outer surface of polygonal shape designed to improve gripping of the device by a user.

5. The device according to claim 1, wherein the hollow cylindrical body has a rear end portion which defines a seat for housing said sealing bush.

6. The device according to claim 1, wherein said sealing bush has at least one interlocking coupling means configured to co-operate with complementary interlocking coupling means formed in the hollow cylindrical body.

7. The device according to claim 1, wherein said interlocking coupling means of the sealing bush consist of a pair of grooves formed on an outer surface of the sealing bush and said complementary interlocking coupling means of the hollow cylindrical body consist of a rib formed on an inner surface of the rear end portion of the hollow cylindrical body, or vice versa.

8. The device according to claim 1, also comprising a slider being coupled with the rod.

9. The device according to claim 8, wherein said slider is coupled at a free end of the rod and comprises a hollow body which defines a seat for housing said free end of the rod.

10. The device according to claim 9, wherein said slider has at least one interlocking coupling means configured to co-operate with complementary interlocking coupling means formed in the rod.

11. The device according to claim 10, wherein said interlocking coupling means of the slider consist of a pair of grooves formed on an inner surface of the seat and said complementary interlocking coupling means of the rod consist of a pair of ribs formed at the free end of the rod, or vice versa.

12. The device according to claim 3, wherein the front end portion has an outer surface of polygonal shape designed to improve gripping of the device by a user.

13. The device according to claim 2, wherein the hollow cylindrical body has a rear end portion which defines a seat for housing said sealing bush.

14. The device according to claim 5, wherein said sealing bush has at least one interlocking coupling means configured to co-operate with complementary interlocking coupling means formed in the hollow cylindrical body.

15. The device according to claim 8, wherein said slider has at least one interlocking coupling means configured to co-operate with complementary interlocking coupling means formed in the rod.

16. The device according to claim 1, wherein when the shoulder abuts against the first mechanical stop, the shoulder is prevented from further movement toward the rear end of the hollow cylindrical body.

17. The device according to claim 1, wherein a Luer-lock fitting is provided on a front end portion of the hollow cylindrical body for engagement/disengagement of the medical device onto/from a bottle or vial containing the medical product to be aspirated.

18. The device according to claim 1, wherein the length of the one portion of the rod is set so that the maximum volume for the medical product within the body is equal to approximately 2-3 drops.

19. The device according to claim 18, wherein the 2-3 drops are equal to about 135 mm$^3$.

* * * * *